United States Patent
Göbel et al.

(10) Patent No.: US 10,393,650 B2
(45) Date of Patent: Aug. 27, 2019

(54) SYSTEM AND METHOD FOR DETERMINING CHARACTERISTICS OF AN OBJECT OR A SAMPLE

(71) Applicant: FRAUNHOFER-GESELLSCHAFT ZUR FÖRDERUNG DER ANGEWANDTEN FORSCHUNG E.V., München (DE)

(72) Inventors: Thorsten Göbel, Berlin (DE); Roman Dietz, Berlin (DE)

(73) Assignee: FRAUNHOFER-GESELLSCHAFT ZUR FÖRDERUNG DER ANGEWANDTEN FORSCHUNG E.V., München (DE)

( * ) Notice: Subject to any disclaimer, the term of this patent is extended or adjusted under 35 U.S.C. 154(b) by 0 days.

(21) Appl. No.: 15/757,618

(22) PCT Filed: Sep. 15, 2016

(86) PCT No.: PCT/EP2016/071889
§ 371 (c)(1),
(2) Date: Mar. 5, 2018

(87) PCT Pub. No.: WO2017/046278
PCT Pub. Date: Mar. 23, 2017

(65) Prior Publication Data
US 2018/0348124 A1    Dec. 6, 2018

(30) Foreign Application Priority Data
Sep. 15, 2015    (EP) .................... 15185323

(51) Int. Cl.
*G01N 21/3581*    (2014.01)
*G01N 21/47*    (2006.01)
(Continued)

(52) U.S. Cl.
CPC ..... *G01N 21/3581* (2013.01); *G01N 21/3151* (2013.01); *G01N 21/4795* (2013.01); *H04B 10/505* (2013.01)

(58) Field of Classification Search
CPC .. H04B 10/505; H04B 10/50; G01N 21/3581; G01N 21/47; G01N 21/3586; G01N 21/4795; G01N 21/33–39; G01N 21/3151
(Continued)

(56) References Cited

U.S. PATENT DOCUMENTS 4,935,628 A     6/1990  Martin et al.
2004/0130704 A1*  7/2004  Beller ............... G01N 21/4795
                                          356/73.1
(Continued)

FOREIGN PATENT DOCUMENTS

DE    10 2006 012 715 A1    9/2007
EP         2509173 A1    10/2012
(Continued)

OTHER PUBLICATIONS

Extended European Search Report dated Mar. 18, 2016 as received in Application No. 15185323.1.
(Continued)

*Primary Examiner* — David P Porta
*Assistant Examiner* — Meenakshi S Sahu
(74) *Attorney, Agent, or Firm* — Maschoff Brennan

(57) ABSTRACT

It is provided a system for determining characteristics of an object or a sample comprising at least a first and a second transmitter unit, wherein the first transmitter unit is configured for transmitting first electromagnetic waves towards the object and the second transmitter unit is configured for transmitting second electromagnetic waves towards the object; at least one receiver unit) for receiving electromagnetic waves from the object, the receiver unit generating a
(Continued)

receiver signal upon receipt of the electromagnetic waves from the object. The first and the second transmitter unit is configured in such a way that the first and the second electromagnetic waves are modulated differently in such a way that by demodulating the receiver signal, a portion of the receiver signal evoked by the first electromagnetic waves can be separated from a portion of the receiver signal evoked by the second electromagnetic waves. The system comprises an evaluating unit.

10 Claims, 1 Drawing Sheet

(51) Int. Cl.
G01N 21/31 (2006.01)
H04B 10/50 (2013.01)
(58) Field of Classification Search
USPC .................................................. 250/341.8
See application file for complete search history.

(56) References Cited

U.S. PATENT DOCUMENTS

2007/0228280 A1 10/2007 Mueller
2009/0279773 A1 11/2009 Gan et al.
2009/0314943 A1* 12/2009 Breit .................. G01N 21/3581
  250/341.1
2010/0067918 A1* 3/2010 Federici ............. G02B 6/12004
  398/158
2010/0080505 A1 4/2010 Sartorius et al.
2010/0171835 A1 7/2010 Kasai et al.
2010/0295725 A1 11/2010 Krozer
2013/0320215 A1 12/2013 Park et al.

FOREIGN PATENT DOCUMENTS

| JP | 1141338 A | 6/1989 |
| JP | 2009075070 A | 4/2009 |
| JP | 2009543036 A | 12/2009 |
| JP | 2013113840 A | 6/2013 |
| WO | 2006/123163 A1 | 11/2006 |

OTHER PUBLICATIONS

Japanese Office Action issued in corresponding application No. 2018-532824, dated Apr. 2, 2019.

* cited by examiner

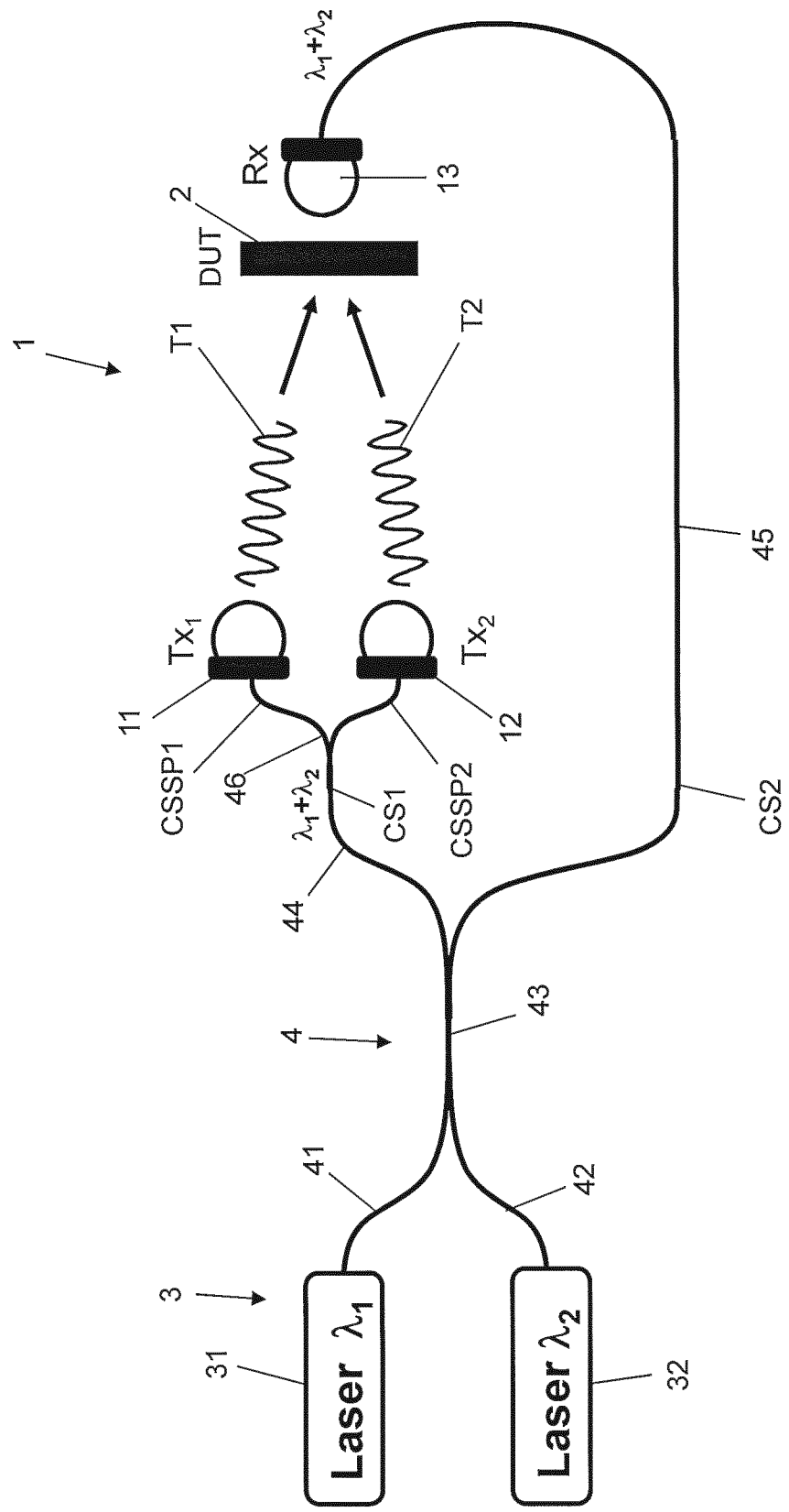

SYSTEM AND METHOD FOR DETERMINING CHARACTERISTICS OF AN OBJECT OR A SAMPLE

CROSS-REFERENCE TO A RELATED APPLICATION

This application is a National Phase Patent Application of International Patent Application Number PCT/EP2016/071889, filed on Sep. 15, 2016, which claims priority of European Patent Application 15185323.1, filed on Sep. 15, 2015.

BACKGROUND

The invention relates to a system for determining characteristics of an object or a sample and a method for determining characteristics of an object or a sample.

Electromagnetic radiation is widely used for non-destructive testing of materials and objects. For example, terahertz radiation is used having a frequency of e.g. approximately 100 GHz to 10 THz. Many modern materials such as polymers, ceramics and compound materials are at least to some extent transparent for that kind of radiation such that for example defects (and the depth of defects) and/or layer thicknesses can be determined using such electromagnetic waves.

However, most terahertz systems use pulsed terahertz radiation, wherein using the transmission time of the pulses, the location of origin of the pulses can be determined such that spatially resolved measurements are possible. These measurements thus can be used e.g. for providing three-dimensional reconstructions of an object. The pulsed systems, however, only allow spatially limited, punctual measurements or require long acquisition times if larger objects shall be investigated.

SUMMARY

The problem to be solved by the invention is to provide a system and a method permitting the measurements to be carried out in a simpler and more flexible way.

According to the invention, a system for determining characteristics of an object or a sample is provided, the system comprising:
- at least a first and a second transmitter unit, wherein the first transmitter unit is configured for transmitting first electromagnetic waves towards the object and the second transmitter unit is configured for transmitting second electromagnetic waves towards the object;
- at least one receiver unit for receiving electromagnetic waves from the object, the receiver unit generating a receiver signal upon receipt of the electromagnetic waves from the object, wherein
- the first and the second transmitter unit is configured in such a way that the first and the second electromagnetic waves are modulated differently in such a way that by demodulating the receiver signal, a portion of the receiver signal evoked by the first electromagnetic waves can be separated from a portion of the receiver signal evoked by the second electromagnetic waves; and
- an evaluation unit configured for generating a two-dimensional and/or a three-dimensional reconstruction of the object using the receiver signal.

Thus, according to the invention, by means of modulating the first and the second electromagnetic waves differently, the portions of the receiver signal that go back to the first electromagnetic waves (transmitted by the first transmitter unit) and the portions of the receiver signal that go back to the second electromagnetic waves (generated by the second transmitter unit) can be identified. Therefore, if the locations of the first and the second transmitter unit and the receiver unit relative to one another and the transmission and/or receiving characteristics (e.g. the transmission and receiving direction, respectively) of the transmitter units and the receiver unit, respectively, and thus the propagation paths of the electromagnetic waves are known, characteristics of the object can be assigned to certain locations of the object. Thus, spatial reconstructions of the object (e.g. of its contours) or other spatially resolved characterizations of the object are possible. For example, the amplitude and/or the phase of the receiver signal is evaluated in order to determine characteristics of the object, e.g. the presence and/or the location of a defect. Further, the system according to the invention might be used for determine characteristics of a (e.g. liquid) sample, e.g. for determining a composition and/or concentration of the sample.

Generally, the system according to the invention may be employed for non-destructive and contactless testing of components (e.g. coatings), for example for use in industrial applications. Testing can be carried on electrically conductive components or component parts as well as on non-conductive components such as fiber-reinforced materials (e.g. fiber-reinforced plastics). Further, optically opaque materials can be investigated. The system according to the invention moreover may permit temperature independent measurements and the analysis of multi-layer structures (in particular with a high spatial resolution, e.g. in the micrometer range). Further, components might be tested that allow access from one side only. It is also possible to investigate moving object such as components (e.g. coated fiber-reinforced components) in a production line.

The first and/or the second transmitter unit may comprise a radiation transmitter for generating electromagnetic radiation and a modulation unit configured for imprinting a modulation onto the electromagnetic radiation.

In particular, the first and the second transmitter unit are configured and arranged in such a way that the first and the second electromagnetic waves interact with the object, wherein because of that interaction, electromagnetic waves propagate from the object towards the receiver unit. For example, the first and/or the second electromagnetic waves are at least partially absorbed and/or reflected by the object, wherein the transmitted portion and/or the reflected portion of the first and/or the second electromagnetic waves is at least partially detected by the receiver unit.

It is noted that the frequency of the first and the second electromagnetic waves does not have to be constant. For example, the frequency of the first and/or the second electromagnetic waves is varied during the measurement. It is possible e.g. that the frequency of the electromagnetic waves is varied within a certain frequency range (e.g. using a ramp-like variation of the frequency). This means, if the first and the second electromagnetic waves are modulated as described above, a carrier frequency of the first and/or the second electromagnetic waves may be varied.

According to another embodiment of the invention, the first transmitter is configured in such a way that the first electromagnetic waves are modulated with a first modulation frequency and the second electromagnetic waves are modulated with a second modulation frequency, the first modulation frequency being different from the second modulation frequency. Because of the different modulation frequencies, the portion of the receiver signal caused by the first electromagnetic waves can be distinguished from the portion of the receiver signal caused by the second electromagnetic waves.

For example, the first and the second transmitter unit are configured in such a way that the first and/or the second electromagnetic waves are modulated in amplitude, frequency and/or phase. In particular, different modulation frequencies are used as mentioned above. However, it is noted that the invention is not restricted to a certain modulation scheme such that modulation methods other than amplitude, frequency and/or phase modulation could be employed.

It is further noted that the direction of the emitted electromagnetic waves might be varied during a measurement in order to scan the object. Further, as already set forth above the carrier frequency might be varied during the measurement (e.g. for each measurement location) as known e.g. from radar detection.

According to another variant of the invention, the first and/or the second transmitter unit are configured for generating terahertz waves. In particular, the first and/or the second transmitter is configured for generating electromagnetic waves in the frequency range of 100 GHz to 10 THz. Of course, other frequencies or frequency ranges could be used.

Moreover, the first and/or the second transmitter unit may be configured for transmitting continuous first and second electromagnetic waves ("cw" waves), respectively. For example, the transmitter units are optoelectronic devices that upon receiving an optical beat signal generate terahertz radiation. The optical beat signal may be created by superimposing the radiation of two lasers having slightly different wavelengths, wherein the laser outputs cw radiation such that cw terahertz radiation is generated. The use of continuous first and second electromagnetic waves e.g. allows the simultaneous detection of larger areas and thus provides shorter measurement times if larger objects are investigated.

According to another variant of the invention, the system might also comprise a demodulation device for demodulating the receiver signal. The demodulated receiver signal is used for assigning portions to either the first or the second electromagnetic waves as explained above.

The system according to the invention further comprises an evaluation unit for determining characteristics of the object by means of the receiver signal. For example, the evaluation unit is realized by a programmed device such as a programmed computer or a programmed microprocessor. The evaluation unit uses the demodulated receiver signal and analysis the amplitude and/or phase of the receiver signal portions and e.g. generates information on the interaction of the first and the second electromagnetic waves with the object (e.g. along the propagations paths through the object).

Moreover, the evaluation unit is configured for generating a two-dimensional and/or is three-dimensional reconstruction of the object using the receiver signal. It is also possible that the evaluation unit is configured for generating a plurality of two-dimensional slices of the object and for reconstructing a three-dimensional representation of the object using the two-dimensional slices similarly to a tomography system (i.e. using tomography algorithms). Accordingly, the system according to the invention might be a tomography system.

Further, the system according to the invention may comprise a beat signal generation source for generating an optical beat signal as already mentioned above. Further, the system may comprise an optical transmission arrangement for transmitting the optical beat signal to the first and the second transmitter unit. The first and/or the second transmitter unit may be configured to generate terahertz waves upon receiving the optical beat signal. Similarly, the receiver unit may receive a portion of the optical beat signal via the optical transmission arrangement, wherein the receiver signal is generated using that portion of the optical beat signal.

For example, the optical transmission arrangement splits the optical beat signal, which is created by superimposing (e.g. using a combiner) the radiation of two laser, in at least two partial beat signals, wherein one of the partial beat signals is supplied to the first and/or the second transmitter unit and the other partial beat signals is supplied to receiver unit. Further, the optical transmission arrangement may comprises a phase changing device for changing the phase of at least one of the partial beat signals. The radiation of the lasers, the optical beat signal and the partial optical beat signals may be transmitted via optical waveguides (e.g. optical fibres).

Suited optical beat signal generation sources are described, for example, in US patent specification 2010/0080505 A1 and in a European patent application published under EP 2 509 173 A1, wherein those patent applications with respect to the general design of the beat signal generation source, the transmitter units and the receiver unit are incorporated by reference herewith. In particular, the transmitter units and/or the receiver unit comprises an optically sensitive and fast semiconductor (photoconductor) for receiving the optical beat signal, the photoconductor being coupled to an antenna. The detection of terahertz waves using the receiver unit is e.g. carried out employing homodyne detection. It noted that the invention, of course, also covers transmitter and receiver units that generate/detect the electromagnetic waves (in particular terahertz waves) fully electronically (i.e. without using an optical beat generation source).

Further, the first and the second (e.g. terahertz) transmitter unit and/or the (e.g. terahertz) receiver unit belong to an array comprising further transmitter and/or receivers. It is also possible that a transmitter array comprising a plurality (more than two) of transmitter units and/or a receiver array comprising a plurality of receiver units are provided. However, a combined array may be used that comprises both a plurality of transmitter units and a plurality of receiver units. The transmitter/receiver array (antenna array) may be used for investigating larger objects such as automotive or airplane parts and/or for increasing the measurement speed. In particular, the transmitter and/or the receiver array is configured for transmitting/receiving continuous terahertz waves. A pulsed operation of transmitter and/or the receiver arrays might be expensive and thus may make industrial applications of pulsed array systems difficult.

The invention also relates to a method for determining characteristics of an object or a sample, in particular using a system as describe above, the method comprising the steps of:
  transmitting first electromagnetic waves towards the object;
  transmitting second electromagnetic waves towards the object;
  receiving electromagnetic waves from the object and generating a receiver signal upon receipt of the electromagnetic waves from the object,
  modulating the first and the second electromagnetic waves differently in such a way that by demodulating the receiver signal, a portion of the receiver signal evoked by the first electromagnetic waves can be separated from a portion of the receiver signal evoked by the second electromagnetic waves; and generating a two-dimensional and/or a three-dimensional reconstruction of the object using the receiver signal.

The method may also comprise evaluating the receiver signal as set forth above with respect to the system according to the invention. Of course, embodiments of the systems described above can be used analogously for refining the method according to the invention.

DETAILED DESCRIPTION

An embodiment of the invention is explained hereinafter with reference to FIG. 1.

FIG. 1 shows a system 1 according to an embodiment of the invention, system 1 being configured for determining characteristics of an object (device under test—DUT 2). The system 1 comprises a first and a second terahertz transmitter unit 11, 12, wherein the first terahertz transmitter unit 11 is configured for transmitting first electromagnetic waves in the form of first continuous (and coherent) terahertz waves T1 and the second transmitter unit 12 is configured for generating second electromagnetic waves in the form of continuous (and coherent) second terahertz waves T2. Both, the first and the second terahertz waves T1, T2 are transmitted towards DUT 2.

The system 1 further comprises a terahertz receiver unit 13 for receiving electromagnetic waves from DUT 2, wherein the receiver unit 13 generates an electrical receiver signal upon receipt of electromagnetic waves from DUT 2. According to the drawing, the receiver unit 13 is arranged behind the DUT 2 such that it will mainly or exclusively detect portions of the terahertz waves T1 and T2 that are transmitted through DUT 2. However, it is also possible that the receiver unit 13 is arranged in such a way that it receives reflected portions of terahertz waves T1 and T2 or both reflected and transmitted portions of terahertz waves T1 and T2. Further, the receiver unit 13 might also detect other radiation evoked by terahertz waves T1, T2 in DUT 2 such as scattered or fluorescence radiation.

The terahertz transmitters 11, 12 are optoelectronic devices that convert an optical beat signal into terahertz waves. Accordingly, system 1 comprises a beat signal generation source 3 comprising a first and a second laser 31, 32 producing optical radiation (λ1, λ2) with a slight shift in frequency. The optical radiation of lasers 31, 32 is coupled into optical fibers 41, 42 of an optical transmission arrangement 4 and superimposed in a combiner 43. A first portion CS1 of the combined signal is supplied to the terahertz transmitters 11, 12 via an optical fiber 44 and a second portion CS2 is supplied to the terahertz receiver unit 13 via an optical fiber 45. The first portion CS1 of the combined signal is split into two sub-portions CSSP 1 and CSSP 2 supplied to the first and the second terahertz transmitters 11, 12, respectively.

The terahertz transmitters 11, 12 generate terahertz radiation upon receipt of the signals CSSP 1 and CSSP 2 as in principle known from the prior art. Further, the terahertz receiver unit 13 generates an electrical signal upon receipt of terahertz waves and the combined signal portion CS2. The principle design of e.g. the beat signal generation source 3, the transmitters 11, 12 and the receiver unit 13 is described, for example, in US patent publication 2010/0080505 A1 and in the European patent application published under EP 2 509 173 A1, already mentioned above.

The first and second terahertz waves T1, T2 emitted by the first and the second terahertz transmitter 11, 12 carry an identifier that allows to distinguish between portions of the receiver signal that are evoked by the first terahertz waves T1 (e.g. reflected and/or transmitted portions of terahertz waves T1 generated by the first terahertz transmitter 11) and portions of the receiver signal that are evoked by the second terahertz waves T2 (e.g. reflected and/or transmitted portions of terahertz waves T2 generated by the second terahertz transmitter 12). The identifier might be realized by modulating both the first and the second terahertz waves T1, T2, i.e. the emitted terahertz waves T1, T2 comprise a modulated carrier wave, wherein different modulation parameters such as different modulation frequencies are used.

This different modulation of the first and the second terahertz waves T1, T2 also shows in the receiver signal such that by demodulating the receiver signal, a portion of the receiver signal that goes back to the first terahertz waves T1 can be separated from a portion of the receiver signal that goes back to the second terahertz waves T2. As the geometric relationship between the terahertz transmitter units 11, 12 and the receiver unit 13 is known (e.g. the distance between the transmitter units 11, 12 and the receiver unit 13 and the propagation direction of the terahertz waves T1, T2), the location of the interaction between the terahertz waves T1, T2 and the DUT 2 is known. Thus, different portions of the receiver signal can be assigned to different locations of the DUT 2 such that properties (characteristics) of DUT 2 determined by means of the receiver signal can be assigned to certain locations of DUT 2. Using 1 system 1 thus may permit to determine a contour of DUT 2 or other geometric parameters as already set forth above. For example, it might be possible to generate a two-dimensional or three-dimensional (e.g. tomography-like) image reconstruction of DUT 2.

Although the embodiment of the invention illustrated in the drawing is related to the optoelectronic generation of terahertz waves T1, T2, the invention is, of course, not restricted to a certain method of producing the terahertz waves. For example, the system according to the invention may also employ fully electronic transmitters and/or receivers.

The invention claimed is:

1. A system for determining characteristics of an object or a sample, comprising:
   at least a first and a second transmitter unit, wherein the first transmitter unit is configured for transmitting first electromagnetic waves towards the object and the second transmitter unit is configured for transmitting second electromagnetic waves towards the object; and
   at least one receiver unit for receiving electromagnetic waves from the object, the receiver unit generating a receiver signal upon receipt of the electromagnetic waves from the object, wherein:
      the first and the second transmitter unit are configured in such a way that the first and the second electromagnetic waves are modulated differently in such a way that by demodulating the receiver signal, a portion of the receiver signal evoked by the first electromagnetic waves can be separated from a portion of the receiver signal evoked by the second electromagnetic waves, wherein the locations of the first and the second transmitter unit and the receiver unit relative to one another and the transmission or receiving characteristics of the transmitter units or the receiver unit, respectively, are known, and an evaluation unit configured for generating a two-dimensional and/or a three-dimensional reconstruction of the object using the receiver signal.

2. The system as claimed in claim 1, wherein the first transmitter unit is configured in such a way that the first electromagnetic waves are modulated with a first modulation frequency and the second transmitter unit is configured in such a way the second electromagnetic waves are modulated with a second modulation frequency, the first modulation frequency being different from the second modulation frequency.

3. The system as claimed in claim 1, wherein the first and the second transmitter unit are configured in such a way that the first and/or the second electromagnetic waves are modulated in amplitude, frequency and/or phase.

4. The system as claimed in claim 1, wherein the first and/or the second transmitter unit is configured for generating terahertz waves.

5. The system as claimed in claim 1, wherein the first and/or the second transmitter unit is configured for transmitting continuous first and second electromagnetic waves, respectively.

6. The system as claimed in claim 1, further comprising a demodulation device for demodulating the receiver signal.

7. The system as claimed in claim 1, further comprising a beat signal generation source for generating an optical beat signal.

8. The system as claimed in claim 7, further comprising an optical transmission arrangement for transmitting the optical beat signal to the first transmitter unit, the second transmitter unit and/or the receiver unit.

9. The system as claimed in claim 1, wherein the first and the second transmitter unit and/or the receiver unit belong to an array comprising further transmitter units and/or receiver units.

10. A method for determining characteristics of an object or a sample, wherein the method comprising the steps of:
transmitting first electromagnetic waves towards the object;
transmitting second electromagnetic waves towards the object;
receiving electromagnetic waves from the object and generating a receiver signal upon receipt of the electromagnetic waves from the object; and
modulating the first and the second electromagnetic waves differently in such a way that by demodulating the receiver signal, a portion of the receiver signal evoked by the first electromagnetic waves can be separated from a portion of the receiver signal evoked by the second electromagnetic waves, wherein the locations of the first and the second transmitter unit and the receiver unit relative to one another and the transmission or receiving characteristics of the transmitter units or the receiver unit, respectively, are known; and
generating a two-dimensional and/or a three-dimensional reconstruction of the object using the receiver signal.

* * * * *